US007008403B1

(12) United States Patent
Mallett

(10) Patent No.: US 7,008,403 B1
(45) Date of Patent: Mar. 7, 2006

(54) INFUSION PUMP AND METHOD FOR USE

(75) Inventor: Scott Mallett, Coto de Caza, CA (US)

(73) Assignee: Cognitive Ventures Corporation, Irvine, CA (US)

( * ) Notice: Subject to any disclaimer, the term of this patent is extended or adjusted under 35 U.S.C. 154(b) by 81 days.

(21) Appl. No.: 10/200,109

(22) Filed: Jul. 19, 2002

(51) Int. Cl.
A61M 37/00 (2006.01)

(52) U.S. Cl. ..................... 604/132; 604/131
(58) Field of Classification Search ............... 604/141, 604/140, 153, 65, 66, 67, 131–133, 143–145, 604/151, 890.1, 891.1, 27, 28, 30, 31, 503–505, 604/93.01; 128/DIG. 12, 13
See application file for complete search history.

(56) References Cited

U.S. PATENT DOCUMENTS

| | | | |
|---|---|---|---|
| 3,756,459 A | 9/1973 | Bannister et al. | |
| 3,894,538 A | 7/1975 | Richter | |
| 4,265,241 A * | 5/1981 | Portner et al. | 604/131 |
| 4,432,468 A * | 2/1984 | Siff et al. | 222/55 |
| 4,443,218 A | 4/1984 | DeCant, Jr. et al. | |
| 4,557,726 A | 12/1985 | Reinicke | |
| 4,666,430 A * | 5/1987 | Brown et al. | 604/141 |
| 4,684,367 A | 8/1987 | Schaffer et al. | |
| 4,718,893 A | 1/1988 | Dorman et al. | |
| 4,955,860 A * | 9/1990 | Ruano | 604/67 |
| 4,969,884 A | 11/1990 | Yum | |
| 5,059,182 A | 10/1991 | Laing | |
| 5,090,963 A * | 2/1992 | Gross et al. | 604/132 |
| 5,207,645 A * | 5/1993 | Ross et al. | 604/141 |
| 5,354,273 A | 10/1994 | Hagen | |
| 5,399,166 A | 3/1995 | Laing | |
| 5,421,208 A | 6/1995 | Packard et al. | |
| 5,476,449 A * | 12/1995 | Richmond | 604/87 |
| 5,492,534 A * | 2/1996 | Athayde et al. | 604/141 |
| 5,527,288 A | 6/1996 | Gross et al. | |
| RE35,501 E | 5/1997 | Ross et al. | |
| 5,704,520 A | 1/1998 | Gross | |
| 5,785,688 A | 7/1998 | Joshi et al. | |
| 5,860,957 A | 1/1999 | Jacobsen et al. | |
| 5,938,636 A | 8/1999 | Kramer et al. | |

(Continued)

Primary Examiner—Manuel Mendez
(74) Attorney, Agent, or Firm—Peter Jon Gluck; Greenberg Traurig LLP

(57) ABSTRACT

A fluid dispensing system provides a non-contact method of monitoring the change in the fluid volume over time. This approach avoids the use of probes or sensors that come into direct contact with the fluid to be dispensed. The system comprises an apparatus comprising three chambers. The first chamber has a fixed volume and contains a pressurized gas. A solenoid valve is used to control the flow of gas from the first chamber into the second. The second chamber is sealed so that the combined mass of air in the first and second chambers remains fixed. The third chamber is adjacent to the second and contains medication in the form of incompressible fluid that is to be administered to a human or animal subject via a suitable delivery port. A piston is disposed between the second and third chambers and is movable responsive to the flow of gas into the second chamber to dispense fluid from the third chamber as desired. By sensing the pressure in the first and second chambers at any point in time, a processor is programmed to calculate the flow rate or dispensed volume of the fluid being delivered using principles derived from the Ideal Gas Law.

10 Claims, 7 Drawing Sheets

U.S. PATENT DOCUMENTS

| | | |
|---|---|---|
| 5,997,501 A | 12/1999 | Gross et al. |
| 6,165,155 A | 12/2000 | Jacobsen et al. |
| 6,186,982 B1 | 2/2001 | Gross et al. |
| 6,280,408 B1 * | 8/2001 | Sipin .............................. 604/65 |
| 6,398,760 B1 * | 6/2002 | Danby ........................ 604/132 |
| 6,413,238 B1 * | 7/2002 | Maget ........................ 604/132 |

* cited by examiner

INFUSION PUMP AND METHOD FOR USE

This invention relates to an apparatus and associated methods for dispensing fluids at a known, measurable rate. More specifically, the present invention pertains to a pump for the intravenous infusion of a medical treatment fluid in which the delivery rate is determined without direct measurement of the fluid flow rate, by using sensed pressure values and the principle of conservation of mass.

Drug delivery devices of varying construction are used to infuse medications or other biologically active substances into human or animal subjects. As used herein, the term "biologically active substance" means all types of medical and biological fluid used in the treatment of humans and animals including but not limited to peptides (such as insulin), analgesics, antiarrhythmics, steroids, hormones, nicotine, vitamins, anti-migraine medicine, anti-coagulants, local anesthetics, vaccines, allergens, muscle relaxants, etc. It should also be recognized that the apparatus is suited for the delivery of fluid into mammals, plants, fish, reptiles, and birds. The dosage levels are typically small and must be maintained over long periods of time in order to sustain a desired effect or result in the subject. A typical application is the administration of pharmaceutical preparations, where the treatment is vital for correct biological activity. The dosage delivery in such instances is often critical, and effective feedback in the form of measured flow rates is seldom available with currently used devices.

A wide variety of approaches have been offered by the prior art to meet the need for a portable device to automatically administer a substance into the vein of a subject. The need for such devices has thus been demonstrated, although the success to date has been limited. This limited success is, at least in part, due to the inability of these devices to provide a simple means to accurately determine the rate at which substance is actually delivered. Prior art devices employ such techniques as mechanical pumps, pressurized gases, pressurized liquids, or gas generating mechanisms. Because the administered substance must be maintained in a sterile environment, a flexible diaphragm is usually employed to separate it from the pump or driving gas.

The requirement for a sterile environment usually precludes direct measurement of either the rate of infusion or the total amount of the medication actually delivered. Instead, the rate of infusion is usually estimated based on the predicted rate of some other event. For instance, some devices use a pressure source in conjunction with a restrictor to regulate the flow of a driving gas. The assumed flow rate can, however, be inaccurate due to variability in pressure, temperature, viscosity of the drug being administered, or other environmental and mechanical factors. Devices using gas-generating mechanisms assume that the flow rate can be determined by correlation to an input such as a voltage. In some cases, other parameters such as body temperature or pulse rate may be used as a feedback mechanism to vary some driving force such as pressure in the cited example. In many instances, however, the precise rate at which a substance must be administered is predetermined without the availability of a feedback mechanism.

U.S. Pat. No. 4,443,218 to DeCant, Jr. et al discloses an implantable infusate pump that utilizes a displacement reservoir to pump an infusate chamber. The displacement reservoir contains a highly viscous fluid that is provided by a second pressure reservoir that utilizes a mechanical pump. By monitoring the pressure differential across a flow restrictor located between the pressure and displacement reservoirs, the flow from the infusate chamber is indirectly measured. While this approach offers a means of measuring the flow of an administered substance, it has several disadvantages in terms of power consumption, overall life, and failsafe operation. Potential leakage of the liquid driver and the use of a mechanical pump are not conducive to sterile applications. The complex arrangement of a mechanical pump with springs and valves to control the pressure inside the pressure reservoir also makes this device more likely to fail as a result of wear.

U.S. Pat. No. 5,527,288 to Gross et al discloses a drug delivery system based on the use of a gas-generating device. An electronic circuit is used to control the time and rate of gas generation into a chamber containing a flexible membrane. Pressure inside the chamber is used to pump a drug contained in a second chamber via the membrane common to both chambers. The generation rate is, however, dependent on environmental factors such as temperature and atmospheric pressure. The lack of a measuring means in this device thus prevents precise determination of the actual drug delivery rate.

A more complex means of controlling the drug delivery rate is also disclosed by Gross et al in U.S. Pat. No. 6,186,982. In this patent, the same basic gas-generating means is used as in U.S. Pat. No. 5,527,288; however, a blocking member is incorporated to compensate for errors induced by temperature and pressure variations. Because of the more complex methods incorporated in this device, it is more prone to malfunction or loss of calibration than that disclosed in U.S. Pat. No. 5,527,288. Errors produced by these or other sources thus preclude an accurate determination of the drug delivery rate using this device.

U.S. Pat. No. 5,421,208 to Packard et al discloses a device for measuring liquid parameters that is directed to peritoneal dialysis, in which a sterile aqueous solution must flow both into and out of the device. Two gas chambers are used to both control and measure the flow of a liquid contained in yet a third chamber. The first of the two gas chambers acts as either a pressure or vacuum source for the second, depending upon the direction of flow required. The second gas chamber acts as a pump for the liquid chamber via a flexible diaphragm dividing the two. The volume of the pump and liquid chamber remains constant during operation. Thus, by determining the volume of the pump chamber, the volume of the liquid chamber is determined. By monitoring the flow of gas from the source chamber and the pressure in the pump chamber, the volume of the pump chamber and, therefore, the liquid chamber can be deduced. One disadvantage of this approach is the need for a flow measurement sensor, which is more complex and prone to failure than sensors used in the art for measuring pressure. There is also a greater possibility for error in the liquid flow measurement due to loss of calibration or malfunction of the gas flow sensor.

SUMMARY OF THE INVENTION

Accordingly, the inventor has developed a: new and novel non-contact approach for determining the delivery rate of a dispensed fluid from an infusion pump in a precise manner.

A system according to the invention provides a non-contact method of monitoring the change in a fluid volume over time through the application of the Ideal Gas Law to measure the volume of an adjacent gas cylinder. The inventive approach avoids the use of probes or sensors that come into direct contact with the fluid. The use of such probes is undesirable in the administration of biologically active substances, since they increase the risk of contamination of the sterile environment in which the fluid must be maintained. Maintaining a sterile environment thus places severe restrictions on the measurement. As a result of these restrictions, prior art systems have generally failed to produce accurate measurements in a simple, compact package. Various methods have been used to establish approximate flow rates based on a presumed reaction rate, but no measurement of actual flow rate is provided to correct for errors introduced by changes in environmental conditions. Devices providing indirect flow measurements have also been suggested, but fail to offer a solution that is simple, reliably accurate, and inexpensive.

The embodiment consists of three chambers. The first chamber contains a high-pressure gas with a fixed volume. A second chamber that is initially at or near atmospheric pressure is located near the first chamber. A solenoid valve is used to control the flow of gas from the first chamber into the second. The second chamber is sealed so that the combined mass of gas in the first and second chambers remains fixed. The third chamber is adjacent to the second and contains medication in the form of incompressible fluid that is to be administered to a human or animal subject via a suitable delivery port.

In a presently preferred embodiment, the first chamber and associated hardware for delivery of gas into the second chamber are contained as a single, reusable housing. The housing for the third chamber is also self-contained and may be either reusable or disposable. The second chamber is defined when the housings of the first and third chambers are interfaced with one another. A piston separates the second and third chambers. The total volume, defined by the second and third chambers, remains fixed during use of the device. As gas is transferred from the first chamber to the second chamber, an increase in the volume of the second chamber results in a corresponding decrease in the volume of the third chamber as a result of movement of the piston. Since the medication is an incompressible fluid, the net result of this process is to deliver a volume of medication that is equivalent to the increase in volume of the second chamber.

Sensors are used to determine the pressure of the gas in the first and second chambers. Since the volume of the first chamber is known and fixed, the ideal gas law, and, specifically, the principle of conservation of mass, is applied to determine combined volume of the second chamber. Since the combined volume of the second and third chambers is known and fixed, the volume of the third chamber is determined from the calculated volume of the second. The flow rate of the medication is determined by calculating the volume of medication in the third chamber at two instances in time and dividing the change in volume by the time between measurements.

It should be noted that the foregoing technique may be used, not just for the particular noted application, but for measuring any unknown volume of a known compressible fluid.

Alternatively, the piston may be replaced with a flexible diaphragm or some other means of providing a movable boundary between the second and third chambers. Preferably, the movable boundary either exerts little or no additional pressure on the gas in the second chamber. If a pressure is introduced by the movable boundary, it must be accounted for during the ideal gas calculation. This boundary may include simply the liquid/gas interface, or may comprise a membrane or piston.

For applications involving the dispensing of medication, the port of the third chamber is suitably formed for attachment of a tube that can be used in conjunction with a Luer fitting. An orifice of fixed flow rate is located in the port. This orifice is used in a unique algorithm to establish an approximate flow rate/dispensed volume that is within the desired range.

Unlike prior art devices, the present invention can be used to determine the precise dispensed volume of medication at any point in time. The total amount of medication delivered and, therefore, the amount of medication still available in the third chamber can be determined at any point in time based on an integration of flow measurements made over time. Because the device has relatively few components, it can be made extremely small, light, and compact. Because the components used are relatively simple, the device can be made extremely reliable without loss of calibration over extended periods of use. Because no sensors, probes, or other hardware are attached to the chamber containing the delivered fluid, the device is well suited to medical applications where sterile environment is critical. Finally, because the electrical components are a microprocessor, solenoid valve, two pressure transducers, and, in some preferred embodiments, one or more temperature sensors, the power consumption is extremely small.

In one aspect of the invention, there is provided a device for delivering controllable quantities of a fluid, which comprises a first chamber containing a gas, and a second chamber. A flow control device, preferably a valve, and more preferably a solenoid valve, is arranged for transferring the gas from the first chamber to the second chamber. A first sensor is provided for sensing the pressure in the first chamber, and a second sensor is provided for sensing the pressure in the second chamber. A third chamber contains a fluid and a port for delivery of the fluid. A boundary, preferably a piston, but also possibly a membrane or simply the interface between the gas and the fluid, separates the second chamber from the third chamber. The boundary moves as the gas is transferred from the first chamber into the second chamber, thus expelling the fluid through the port. A processor is provided for determining the dispensed volume of fluid from the third chamber, based upon the pressures sensed by the first and second pressure sensors. Alternatively, one of the two chamber pressures are sensed directly, and the differential pressure between the two chambers is sensed and used to calculate the pressure in the remaining chamber.

In another aspect of the invention, there is taught a method of measuring an unknown fluid flow rate or dispensed volume, which comprises a step of providing a first chamber containing a gas, and a step of providing a second chamber. Gas is transferred from the first chamber to the second chamber. The pressure in the first chamber is sensed, as is the pressure in the second chamber. A third chamber is provided which contains a fluid to be delivered and a port for delivery of that fluid. A boundary, preferably a piston, is provided to separate the second chamber from the third chamber. The boundary is moved as the gas is transferred from the first chamber into the second chamber, thus expelling the fluid through the port. The method advantageously includes a unique step of calculating the dispensed volume of fluid from the third chamber based upon the pressures sensed in the first chamber and the second chamber.

In still another aspect of the invention, there is disclosed a method for determining an unknown volume of compressible fluid in a chamber, which comprises steps of providing a device having a first chamber and a second chamber, wherein the first chamber contains a gas and has a fixed volume, and transferring the gas from the first chamber to the second chamber. The pressure in each of the first and second chambers is simultaneously sensed, after which the volume of the second chamber is calculated using the pressure values sensed in the first and second chambers and the fixed volume of the first chamber.

In yet another aspect of the invention, there is disclosed a method for determining an unknown volume of compressible fluid in a chamber, which comprises steps of providing a device having a first chamber and a second chamber, wherein the first chamber contains a gas and has a fixed volume, and transferring the gas from the first chamber to the second chamber using a pressure regulator. In this method, the pressure in the first chamber is sensed, after which the volume in the second chamber is calculated using the pressure sensed in the first chamber and the known pressure in the second chamber set by the regulator.

The invention, together with additional features and advantages thereof, may best be understood by reference to the following description taken in conjunction with the accompanying illustrative drawing.

DESCRIPTION OF THE PREFERRED EMBODIMENT

Figure 1:
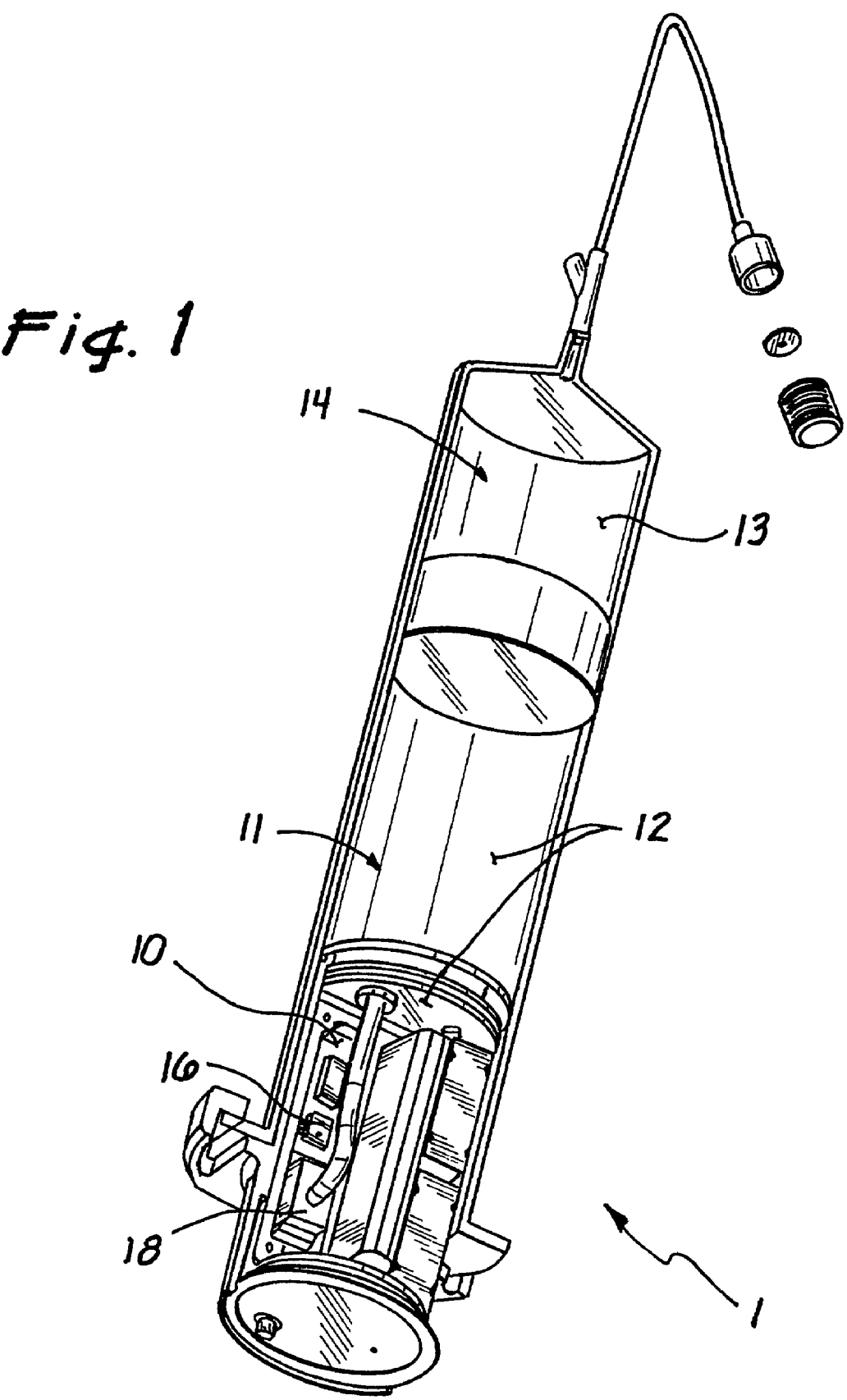
FIG. 1 is a schematic perspective view of one embodiment of the components of the infusion pump of the present invention.

As shown in the drawings for purposes of illustration, the invention is embodied in a novel system to dispense a fluid and measure the fluid delivery rate.

In a preferred embodiment, shown in FIG. 1, the inventive device 1 comprises three chambers. A first chamber 10 and a second chamber 11 contain a gas 12 that is used to pump a fluid 13 contained in a third chamber 14. The fluid 13 is pumped at a controlled rate as the gas 12 in the first chamber 10 enters the second chamber 11. Two pressure probes 16 and 18 sense the pressure in the chambers 10 and 11. By monitoring these two pressures the volume of the second chamber 11 and, consequently, the volume of the third chamber 14 may be accurately determined. By knowing the volume of the third chamber 14, the volume or flow rate therefrom can be determined at any point in time. The resulting device provides a simple and economical method of delivering a fluid. Because the invention has few components, it is very reliable in terms of operation and accuracy. The invention takes advantage of the ideal gas law in an innovative manner that allows fluid flow to be determined without making a direct flow measurement. As a result neither the pump nor the measurement probes come into contact with the fluid, thus making it ideal for medical applications.

Figure 2:
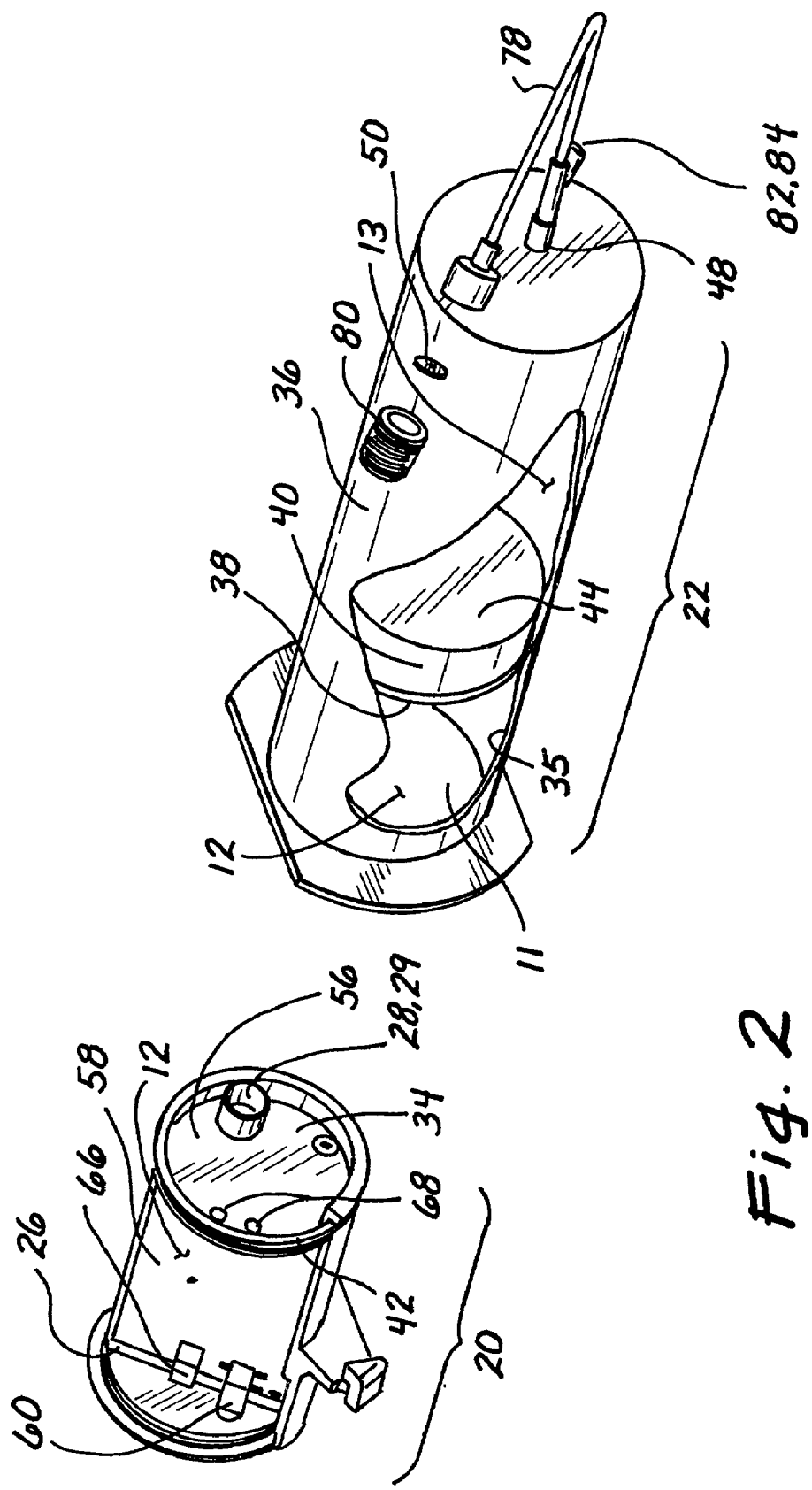
FIG. 2 is a perspective view of the embodiment of FIG. 1, with portions broken away to illustrate internal construction features, in an unassembled state.

More particularly, in a presently preferred embodiment, as shown in FIG. 2, the infusion pump 1 comprises a hardware module 20 and a delivery module 22. Preferably, the hardware module 20 is reusable, which is an attractive feature since its components are relatively expensive. The delivery module 22, on the other hand, is preferably disposable. This disposability is desirable for the delivery module in applications requiring a sterile environment, such as medical applications.

Figure 2A:
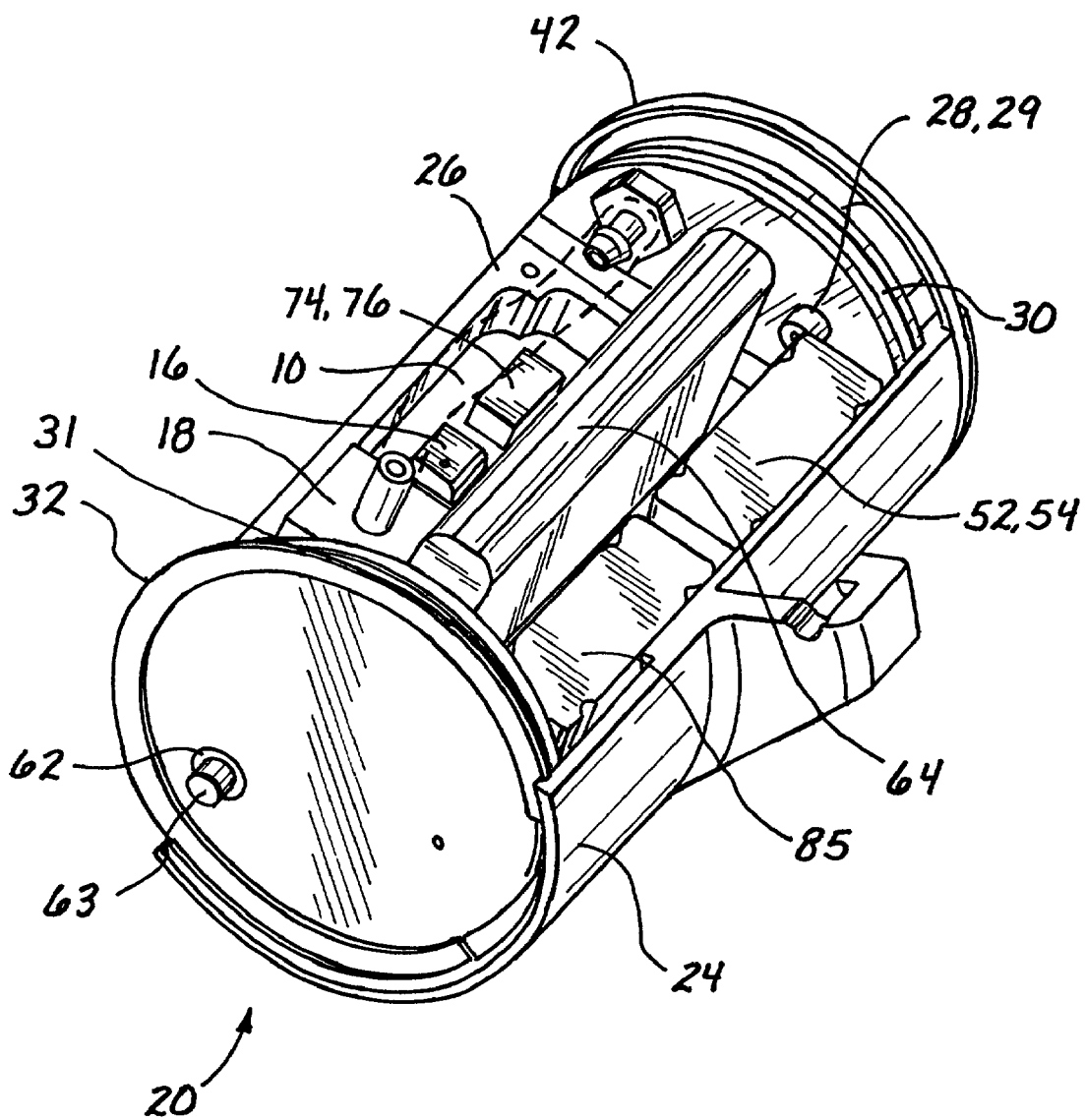
FIG. 2A is a perspective view of the hardware module of the infusion pump shown in FIGS. 1 and 2.

As particularly shown in FIG. 2A, the hardware module 20 and the delivery module 22 together define the three chambers that comprise both the pump and the system for measuring the fluid flow rate. The first chamber 10 is defined by the inner surfaces of a body 24 and a pair of end caps of an insert 26 of the hardware module 20. The first chamber 10 is filled with the gas 12 such as air, nitrogen, or another gas that can be suitably compressible. The first chamber 10 may be charged via a fill port 28 containing a check valve 29 that is used to prevent unwanted leakage of the gas 12 into the second chamber 11. Two o-rings 30, 31 are used on the end caps of the insert 26 to seal the gas 12 inside the first chamber 10. The insert 26 is secured onto the body 24 through the use of a retaining ring 32.

The second chamber 11 is created when the hardware module 20 is inserted into the delivery module 22. The volume of the second chamber 11 is defined by a face 34 of the insert 26, an inner wall 35 of a syringe body 36, and an outer face 38 of a piston 40 located inside and part of the delivery module 22. An o-ring 42 is used to seal the second chamber 11, since the inventive flow rate calculation taught herein assumes that the total mass of the gas 12 in the chambers 10 and 11 remains constant.

The third chamber 14 is defined by the inner wall 35 of the syringe body 36 and an inner face 44 of the piston 40. The third chamber 14 is filled with the fluid 13 to be delivered, which may be a medication or some other biologically active substance. The fluid 13 is delivered to the patient via a fluid port 48. A fluid restrictor 50 is used to establish an approximate fluid flow rate. Various sizes of the fluid restrictor 50 may be provided, depending upon the flow rate and pressure range being used. Optionally, a pressure relief valve may be employed instead of the fluid restrictor 50, which valve is designed to crack at a predetermined pressure. In such an embodiment, boluses of medication are dispensed, rather than a continuous flow.

In order to control the flow of the gas 12 between the chambers 10 and 11, a solenoid valve 52 is attached to a bulkhead 54 of the insert 26. An airflow restrictor 56 may be used in conjunction with the solenoid valve 52 to control the flow of the gas 12. The purpose of the restrictor is to permit the gas to move from the first chamber to the second chamber at a rate which is easily controlled by the software at a particular sampling rate. If the flow is too fast, too much gas will move from the first chamber to the second chamber, causing over-dispensing. On the other hand, if the flow is too slow, the solenoid must remain open longer, diminishing the battery life.

An electronic assembly 58 is provided for the purposes of obtaining information from the pressure probes 16 and 18, and optional temperature sensors, to be discussed hereinbelow, calculating the amount of the fluid 13 delivered, and adjusting the fluid flow rate by controlling the duty cycle of the solenoid valve 52. A mode switch 60 is provided to initiate the various sequences controlled by the printed circuit board assembly 58. A seal 62 and a switch plunger 63 prevent leakage of the gas 12 through the mode switch 60. A battery 64 provides power to the electrical components inside the hardware module 20. An LED 66 is provided to indicate when an error condition has occurred. A set of charging contacts 68 are provided for charging the battery between treatments.

In the preferred embodiment, the pressure probe 16 is used to sense the absolute (PSIA) pressure inside the first chamber 10. In the preferred embodiment, the pressure probe 18 senses the absolute pressure inside the second chamber 11. Alternatively, gauge pressure could be sensed, from which the absolute pressure values could be calculated. However, using gauge transducers referenced to ambient decreases accuracy, relative to the direct usage of absolute (PSIA) transducers, and absolute pressure transducers are accurate for any altitude.

In the preferred embodiment, a first temperature sensor 74 and a second temperature sensor 76 are used to provide the temperature of the gas 12 in the first chamber 10 and the second chamber 11, respectively. The gas temperature is needed in order to make inventive flow rate calculation of the fluid 13. In other embodiments, the first temperature sensor 74, the second temperature sensor 76, or both may be eliminated for applications where the fluid temperature is assumed to be constant, although accuracy will be somewhat reduced.

In the preferred embodiment, the delivery module 22 also incorporates a capillary tube 78 and a Luer fitting 80 for connection to a patient catheter or IV (not shown). A liquid fill port 82 and a check valve 84 are provided to fill the third chamber 14 with the fluid 13. In other embodiments, the delivery module 22, the capillary tube 78, the Luer fitting 80, and the liquid fill port 82 may be substituted or eliminated for applications that do not involve the intravenous infusion of a medical treatment fluid.

A solenoid vent valve 85 is employed in a preferred embodiment, as a failsafe feature for venting all gas (air) from chamber 11, in the event of a malfunction of solenoid 52, in order to prevent any further dispensing of medication.

The delivery module 22 is packaged in a sterile pouch, which is opened by a qualified medical professional or pharmacist. The fluid 13 is infused into the delivery module 22 by the qualified medical professional or pharmacist through the liquid fill port 82. Once filled to the desired volume, the delivery module 22 is bagged and labeled for use. Any volume of fluid, up to the capacity of the pump, can be dispensed.

Once the delivery module 22 is filled, it is transferred to a clinician for connection to the hardware module 20, primed, and connected to the patient. After each use, both the battery 64 and the first chamber gas pressure 10 are recharged for the subsequent use. The target pressure, $P_{target}$, is defined as the pressure in the second chamber 11 required to produce the required fluid flow rate for a given size of the fluid restrictor 50. Initially, the pneumatic charge in chamber 10 is sufficiently high such that when the piston 40 reaches the end of its stroke, the pressure in the first chamber 10 is greater than the $P_{target}$. The initial charge pressure, $P_{1i}$, required in the first chamber 10 is determined as follows: If the volume of the second chamber 11 at the end of its stroke is "X" and the target pressure, $P_2$, is "Y", then the product "XY" must be exceeded by the product of the volume of the first chamber 10 times $P_{1i}$, by some predetermined margin.

Priming:

An initial volume in the second chamber 11 is defined upon insertion of the hardware module 20 into the delivery module 22. Depressing the mode switch 60 initiates the process of bleeding the fluid 13 through the capillary tube 78. Once this process is started, the solenoid valve 52 is energized to allow the gas 12 to pass between the chambers 10 and 11. The increase in pressure of the second chamber 11 produces a force on the piston 40 that, in turn, increases the pressure in fluid the third chamber 14, thus causing the fluid 13 to be ejected via the fluid port 48. Fluid is dispensed from the third chamber 14 until all air in the capillary tube 78 has been displaced by fluid. The unit is now ready for use with a patient.

Figure 3:
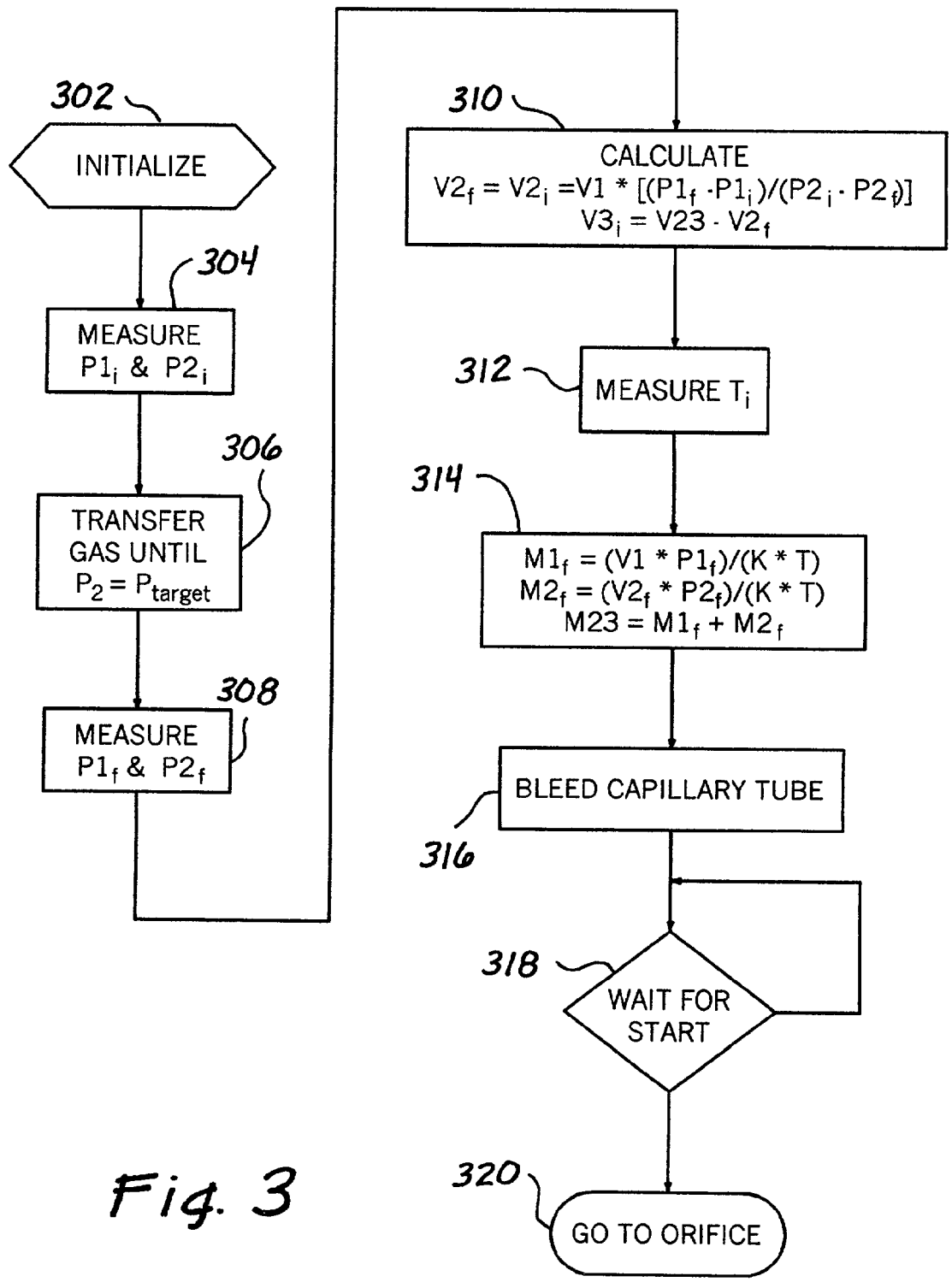
FIG. 3 is a flowchart showing a preferred method of determining the initial fluid volume of the infusion pump of the present invention.

Determination of Initial Fluid Volume:

The initial volume of the second chamber 11 must be determined before the device can be used to accurately monitor the fluid flow rate. In the preferred embodiment, this is accomplished by running the initialization procedure illustrated by the flow chart in FIG. 3. The mode switch 60 is used to begin the initialization procedure. During the initialization procedure, the position of the piston 40 is assumed to remain fixed in order maintain a constant volume, $V_{2i}$, in the second chamber 11.

The initialization procedure starts at reference numeral 302, labeled "INITIALIZE". In step 304, the pressure in the chambers 10 and 11, $P_{1i}$, and $P_{2i}$, are measured using the pressure probes 16 and 18, respectively. The solenoid valve 52 is used at step 306 to transfer a sufficient amount of the gas 12 between chambers 10 and 11 such that the pressure in the second chamber 11 to approximate value of $P_{target}$. The new pressures in the chambers 10 and 11 are again measured at step 308 and labeled $P_{1f}$ and $P_{2f}$, respectively. Because the volume of both chambers was fixed during the transfer of the gas 12, the ideal gas law is used in step 310 to calculate volume, $V_2$, of the second chamber 11 as:

$$V_{2f}=V_{2i}=V_1*[(P_{1f}-P_{1i})/(P_{2i}-P_{2f})] \quad (1)$$

where $V_1$ is the volume of the first chamber 10. Since the first chamber 10 is a fixed volume, the value of $V_1$ is a known constant during the entire operation of the device. The total combined volume of the second chamber 11 and the third chamber 14, $V_{23}$, is also a known constant during the entire operation of the device. The volume of $V_{3f}$ can, therefore, be calculated as:

$$V_{3i}=V_{23}-V_{2f} \quad (2)$$

Knowing the pressures and volumes of the gas 12 in the two chambers, the ideal gas law is again utilized to determine the total mass and its distribution between the two chambers. At step 312 the temperature of the gas 12 by using either the first temperature sensor 74 or the second temperature sensor 76 or both. In another embodiment, the temperature, T, of the gas 12 is assumed to be at the standard room temperature of 20° C., thus precluding the necessity of either first temperature sensor 74 or the second temperature sensor 76. As shown in step 314, the mass in the first chamber 10, $M_{1f}$, and the second chamber 11, $M_{2f}$, is:

$$M_{1f}=(V1*P_{1f})/(K*T) \quad (3)$$

$$M_{2f}=(V_{2f}*P_{2f})/(K*T) \quad (4)$$

where K is the universal gas constant. The total gas mass of the system is simply, $$M_{23}=M_{1f}+M_{2f} \quad (5)$$

The total gas mass, $M_{23}$, is now established and remains constant for all future operations, since the system is closed.

At step 316, the cap at the capillary tube 78 is removed and the pressure in the second chamber 11 causes the fluid 13 to advance down the capillary tube until all the air is pushed out. When the operator has observed the first few drips of fluid come out of the orifice, the flow is stopped by replacing the cap onto the end of the capillary tube 78. Once this initialization is complete, the firmware programmed into the printed circuit board assembly 58 causes the system to go into a wait state, step 318. The step ends once the a signal is received by the user to go to ORIFICE, step 320.

Determination of the Dispense Rate:

After a period of several minutes to several hours in the wait state, the cap is removed from the capillary tube 78, thus initiating the flow of the fluid 13. The Luer fitting 80 is then attached to the patient infusion needle to begin treatment. The operator again uses the mode switch 60 to start the device.

The value of $M_{23}$ calculated during the initialization procedure remains constant for the closed system defined by the chambers 10 and 11.

Figure 4:
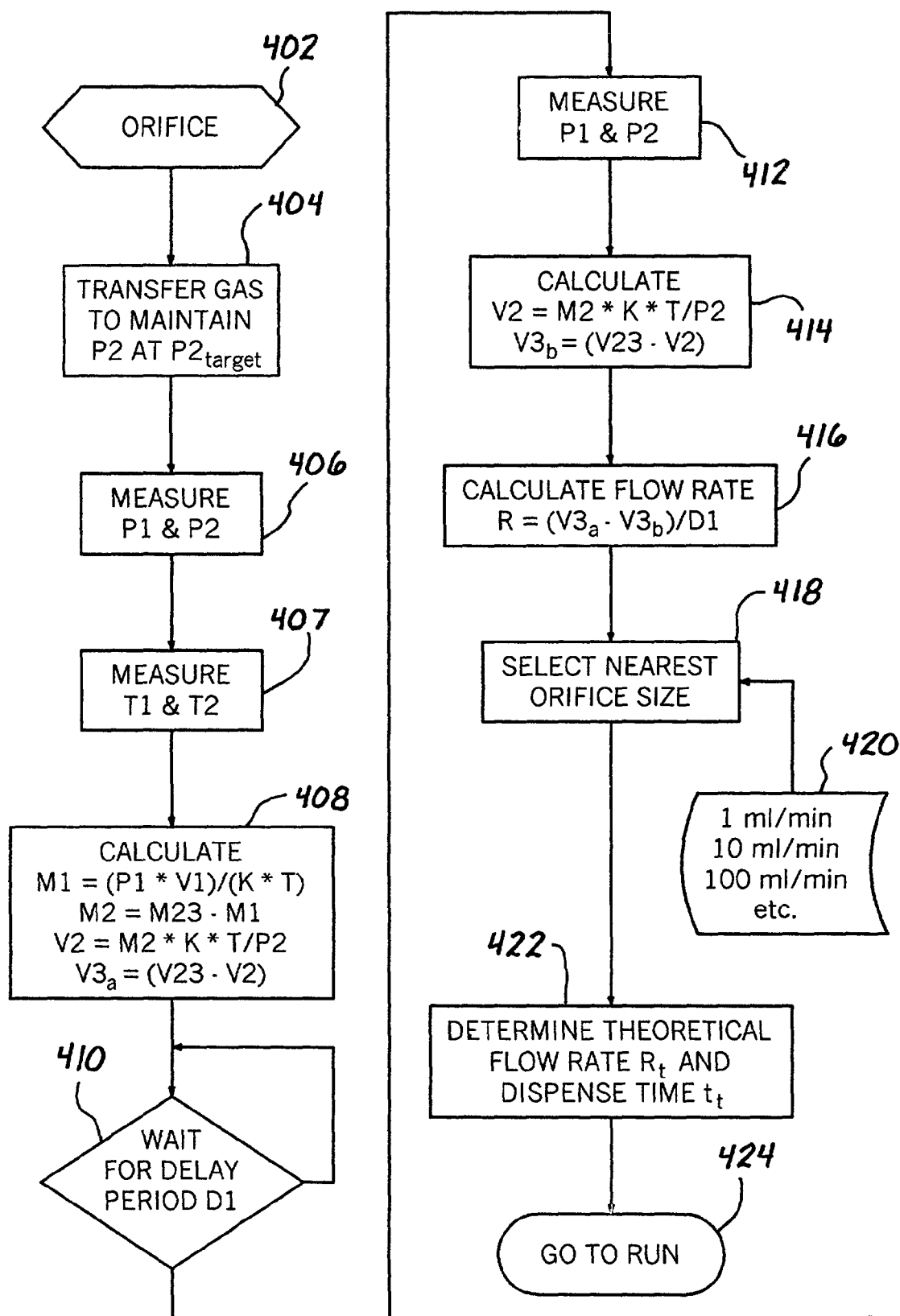
FIG. 4 is a flowchart showing a preferred method of determining the target dispense rate or volume of the infusion pump of the present invention.

When the printed circuit board assembly 58 receives an activation signal, the procedure in FIG. 4 is used to determine the fluid flow rate. The procedure starts at the label "ORIFICE", reference numeral 402. At step 404, the solenoid valve 52 is activated to allow the gas 12 to again flow from the first chamber 10 to the second chamber 11. When the pressure in the second chamber 11 equals approximately $P_{target}$, the solenoid valve 52 is closed. The pressures in the first chamber 10 and the second chamber 11 are measured at step 406 and labeled $P_1$ and $P_2$. The temperature of the gas 12 is measured at step 407 using the first temperature sensor 74, the second temperature sensor 7, or both. Alternative, as discussed supra, if applicable, the temperature T of the gas 12 may be assumed to be at the standard room temperature of 20° C., thus precluding the necessity of either first temperature sensor 74 or the second temperature sensor 76.

The total mass of the gas 12, $M_{23}$, was previously determined at step 314 and remains a known constant. Since the volume of the first chamber 10 is also a known constant, the mass in the first chamber 10 and the second chamber 11 can always be calculated from $P_1$ and T. These calculations are made at step 408 along with the volumes of the second chamber 11 and the third chamber 14:

$$M_1 = (V_1 * P1)/(K*T) \tag{6}$$

$$M_2 = M_{23} - M_1 \tag{7}$$

$$V_2 = M_2 * K * T / P_2 \tag{8}$$

$$V_{3a} = V_{23} - V_2 \tag{9}$$

where $V_{3a}$ is the instantaneous volume of the fluid 13. After a short time delay (step 410), $D_1$, the pressure in the second chamber 11 is again measured at step 412 to determine the amount of the fluid 13 remaining after the time delay. The calculations are made in step 414:

$$V_2 = M_2 * K * T / P_2 \tag{10}$$

$$V_{3b} = V_{23} - V_2 \tag{11}$$

where $P_2$ and $V_2$ have changed from the initial measurement. The flow measurement is now made at step 416:

$$R = (V_{3a} - V_{3b})/D_1 \tag{12}$$

where R is the flow rate. The value for the flow rate is then rounded off to the nearest increment of known orifice sizes, such as 1 ml/hr, 10 ml/hr, or 100 ml/hr (steps 418 and 420). At step 422, the theoretical flow rate, $R_t$, along with the initial fluid volume, $V_{3i}$, are used to compute the theoretical dispense time, $t_t$:

$$t_t = V_{3i}/R_t \tag{13}$$

Once the flow rate has been established, the device enters into the run sequence, step 424.

Figure 5:
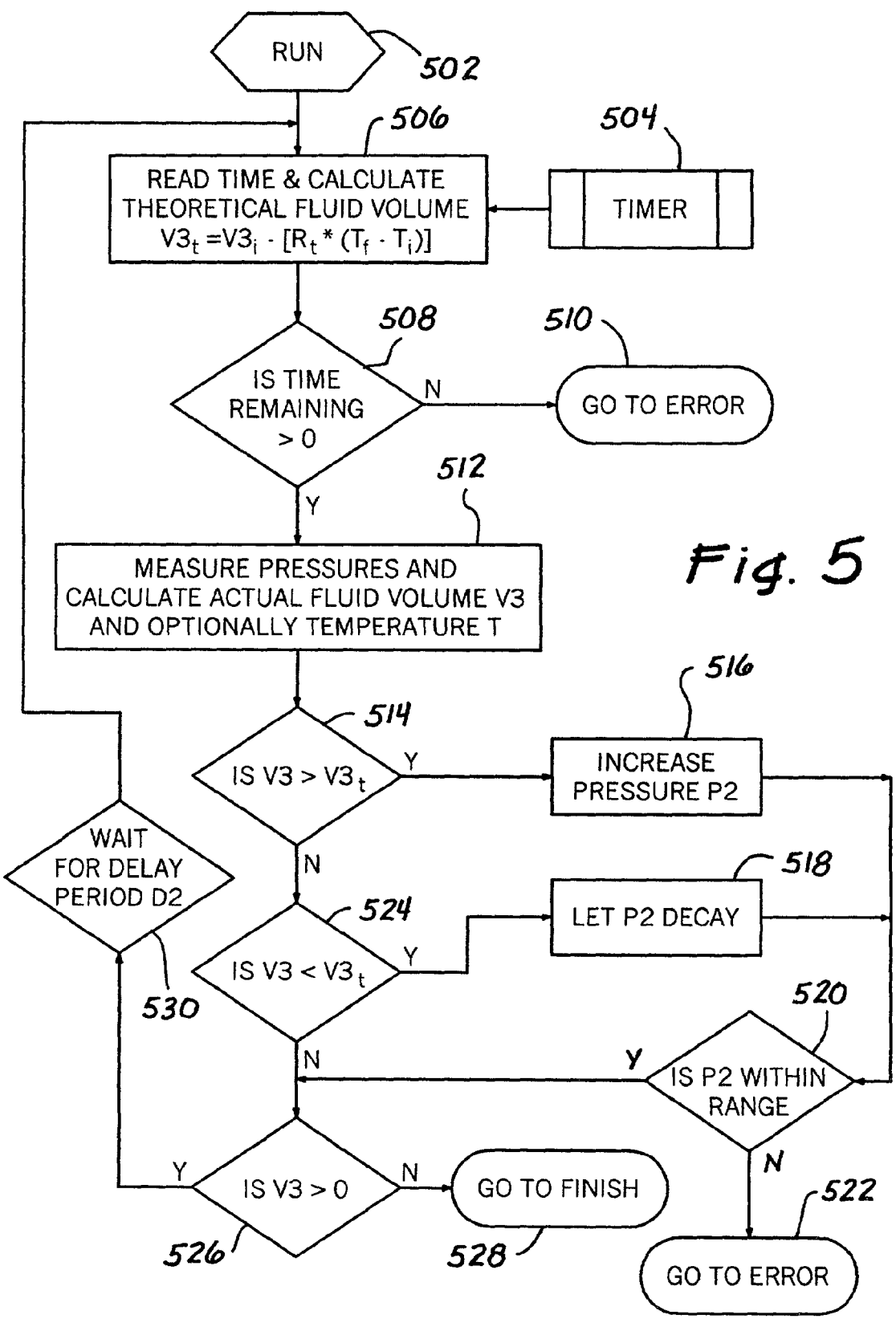
FIG. 5 is a flowchart showing a run sequence for the infusion pump of the present invention.

Run Sequence:

The fluid 13 continues to be delivered to the patient via the run sequence outlined in FIG. 5. The sequence starts operation at label "RUN", reference numeral 502. During the run sequence, the pressure in the second chamber 11 is maintained at approximately $P_{target}$, but the duty cycle of the solenoid valve 52 is varied to "speed up" or "slow down" the dispense rate. In other words, solenoid valve duty cycles may be skipped as desired to maintain the dispense rate in the desired range. It is important to maintain $P_2$ within the desired band to prevent over-dispensing of medication. At predetermined intervals, a timer 504 is used to compute the theoretical fluid volume, $V_{3t}$, based on the elapsed time, $\Delta t$, and the theoretical flow rate $R_t$ at step 506:

$$V_{3t} = V_{3i} - (R_t * \Delta t) \tag{14}$$

At step 508 a check is made to see if the dispense time, $t_t$, has been exceeded. If this time has been exceeded, the ERROR sequence is called in step 510. If there is still time remaining, the pressures in the first chamber 10 and the second chamber 11 are measured in step 512, along with temperature, T, if needed. These values are used in step 512 to calculate the remaining volume of the fluid 13:

$$M_1 = P_1 * V_1 / (k*T) \tag{15}$$

$$M_2 = M_{23} - M_1 \tag{16}$$

$$V_2 = M_2 * k * T / P_2 \tag{17}$$

$$V_3 = V_{23} - V_2 \tag{18}$$

$V_3$ is the actual fluid volume and is compared with the theoretical fluid volume. If $V_3$ is different from the theoretical fluid volume, minor changes are made to the duty cycle of solenoid valve 52 to maintain the required flow rate. This adjustment process is shown in steps 514 to 524 and continues until all the fluid has been dispensed within the theoretical dispense time. If $P_2$ falls outside of a predetermined range, steps 520 and 522 call the ERROR sequence. If $V_3$ falls below a predetermined value, step 528 calls the FINISH sequence. If $V_3$ is above $V_{3min}$, step 530 delays for a predetermined time $D_2$, and begins the sequence again at step 504.

Figure 6:
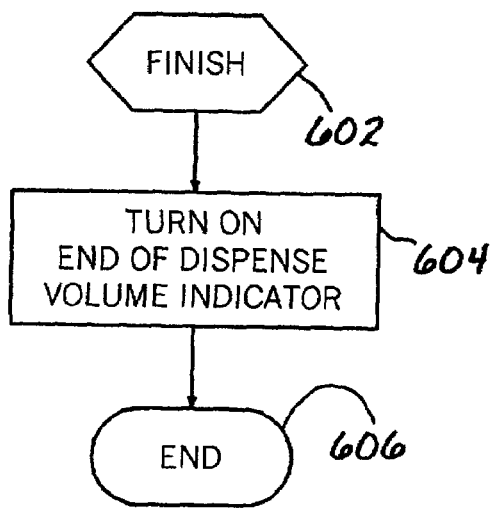
FIG. 6 is a flowchart of the finish sequence for the infusion pump of the present invention.

Finish:

When the fluid falls below the predetermined minimum value, $V_{3min}$, the finish sequence shown in FIG. 6 is called starting at step 602. Step 604 turns on an LED 816 to signal the user that the dispense volume has run out and that the case is over. The system is shut down at step 606.

Figure 7:
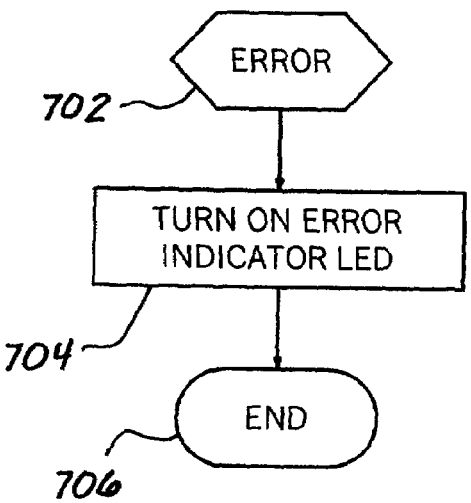
FIG. 7 is a flowchart of the error sequence for the infusion pump of the present invention.
Figure 8:
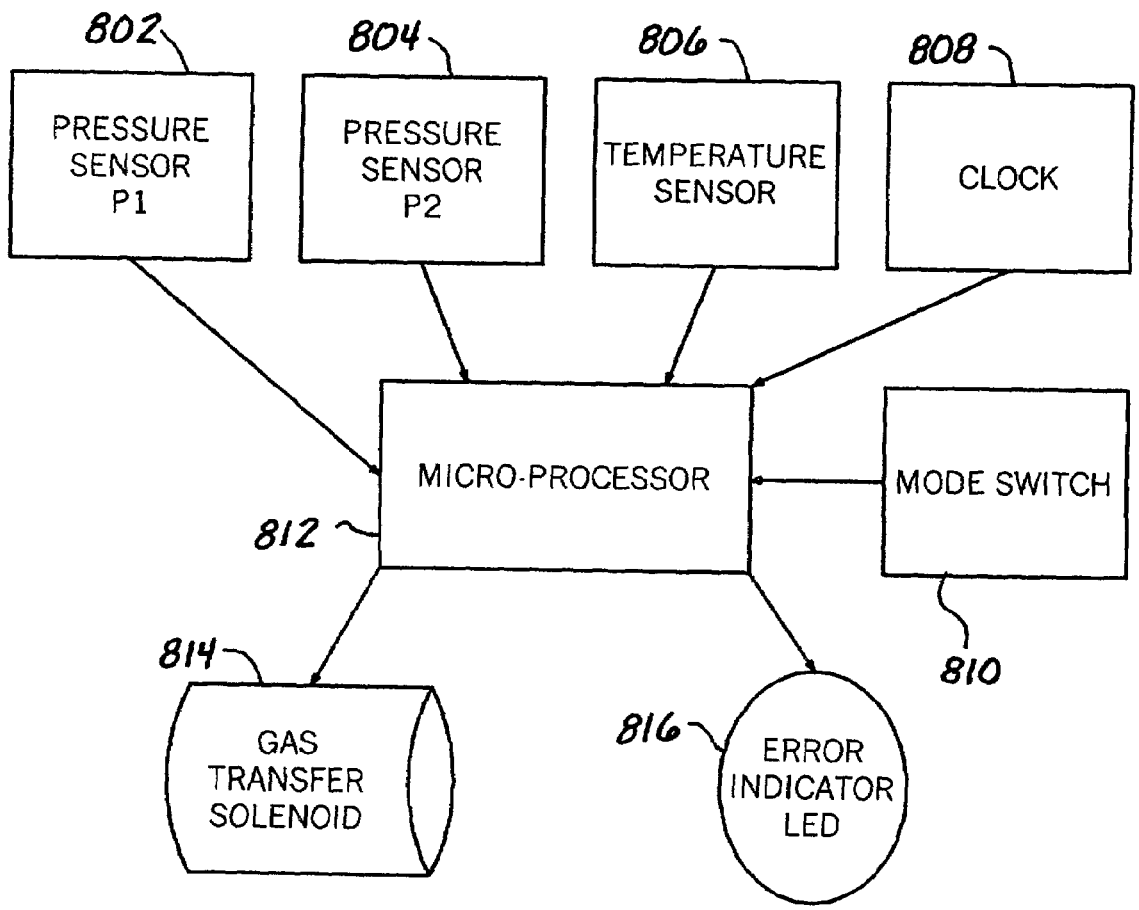
FIG. 8 is a schematic diagram of the control assembly for the infusion pump of the present invention.

Error:

When an error is encountered, the error sequence in FIG. 7 is called starting at step 702. Step 704 turns on an LED 816 to alert the operator of a problem. The system is again shut down at step 706.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A device for delivering controllable quantities of a fluid, comprising, in combination:
   a first chamber having a fixed volume for containing a gas;
   a second chamber;
   a device for transferring said gas from said first chamber to said second chamber;
   a third chamber for containing a fluid, wherein a combined volume of said second and third chambers is fixed;
   solenoid communication vales;
   at least a luer connector;
   a movable boundary disposed between said second and third chambers;
   a dispensing port for dispensing said fluid from said third chamber;
   a pressure sensor for sensing pressure in at least one of said first and second chambers; and,
   a processor for determining the volume of said second chamber.

2. A device for delivering controllable quantities of a fluid, comprising, in combination:
   a first chamber having a fixed volume for containing a gas;
   a second chamber;
   a device for transferring said gas from said first chamber to said second chamber;
   a third chamber for containing a fluid, wherein a combined volume of said second and third chambers is fixed;
   solenoid communication valves;
   at least a luer connector disposed at a port of the third chamber in conjunction with an orifice of fixed flow rate located in the port;
   a movable boundary disposed between said second and third chambers;
   a dispensing port for dispensing said fluid from said third chamber;
   a non-fluid contact pressures sensor for sensing pressure in at least one of said first and second chambers which does not come into contact with subject fluid in the device; and,
   a processor for determining the volume of said second chamber.

3. A device for delivering controllable quantities of a fluid, which comprises:
   a first chamber having a fixed volume for containing a gas;
   a second chamber;
   a device for transferring said gas from said first chamber to said second chamber;
   a third chamber for containing a fluid, wherein a combined volume of said second and third chambers is fixed;
   solenoid communication valves;
   at least a luer connector disposed at a port of the third chamber in conjunction with an orifice of fixed flow rate located in the port;
   a piston disposed between said second and third chambers;
   a dispensing port for dispensing said fluid from said third chambers;
   a non-fluid contact pressure sensor for sensing pressure in at least one of said first and second chambers which does not come into contact with subject fluid in the device; and, a processor for determining the volume of said second chamber, based upon flow through the orifice as defined by an algorithm.

4. The device as recited in claim 1, wherein the gas is compressed air.

5. The device as recited in claim 1, wherein the fluid is a biologically active substance.

6. The device as recited in claim 1, wherein said biologically active substance is a medication.

7. The device as recited in claim 1, wherein the port further comprises:
   a fluid restrictor having known flow characteristics; and said processor determines the instantaneous delivery rate of the fluid in said third chamber using the known restrictor flow characteristics.

8. The device as recited in claim 1, wherein the port further comprises a fill port for refilling said space with a second fluid.

9. The device as recited in claim 1, wherein said boundary comprises a piston.

10. The device as recited in claim 1, wherein said boundary comprises a membrane.

* * * * *